United States Patent [19]

DeVries et al.

[11] Patent Number: 5,416,233
[45] Date of Patent: May 16, 1995

[54] PREPARATION OF VINYLSILANE-BENZOCYCLOBUTENES

[75] Inventors: Robert A. DeVries; Edmund J. Stark, both of Midland, Mich.

[73] Assignee: The Dow Chemical Company, Midland, Mich.

[21] Appl. No.: 186,412

[22] Filed: Jan. 25, 1994

[51] Int. Cl.$^6$ ................................. C07F 7/08
[52] U.S. Cl. ................... 556/479; 556/450; 556/453; 556/456
[58] Field of Search ............... 556/479, 450, 453, 456

[56] References Cited

U.S. PATENT DOCUMENTS

| | | | |
|---|---|---|---|
| 3,404,169 | 10/1968 | Gaignon et al. | 556/479 |
| 3,410,886 | 11/1968 | Joy | 556/479 |
| 3,793,358 | 2/1974 | Bauer et al. | 556/479 |
| 4,579,965 | 4/1986 | Kanner et al. | 556/479 |
| 4,642,329 | 2/1987 | Kirchhoff et al. | 526/284 |
| 4,724,260 | 2/1988 | Kirchhoff et al. | 546/112 |
| 4,812,588 | 3/1989 | Schrock | 556/453 |
| 4,822,930 | 4/1989 | Liu | 570/206 |
| 4,898,961 | 2/1990 | Baile et al. | 556/479 |
| 5,041,595 | 8/1991 | Yang et al. | 556/479 |
| 5,136,069 | 8/1992 | DeVries et al. | 556/453 |
| 5,138,081 | 8/1992 | DeVries et al. | 556/466 |
| 5,243,068 | 9/1993 | DeVries et al. | 560/205 |

OTHER PUBLICATIONS

R. A. DeVries et al., Catalytic Vinylic Coupling Used to make Benzocyclobutene Derivatives—Poster Session, 12th N. American Catalyst Society, May 5–9, 1991.
R. L. Merker et al., The Preparation and Properties of Some Silylmethyl and Silylprpyl Substituted Tin Compounds, pp. 975–976, Aug. 18, 1958.
Edwin P. Plueddemann, Silane Coupling Agents, pp. 32–73, 1982.
J. F. Harrod et al., Hydrosiliation Catalyzed by Group VIII Complexes, Organic Syntheses via Metal Carbonyls, vol. 2, pp. 673–705; 1984.
L. N. Lewis et al., Platinum–Catalyzed Hydrosilylation of Alkynes, 1991, J. Organomet. Chem. vol. 10 pp. 3750–3759.
J. L. Speier, Homogeneous Catalysis of Hydrosilation by Transition Metals, Adv. Organomet. Chem., vol. 17, pp. 407–447, 1979.
R. A. Benkeser et al., The Stereochemistry of the Addition of Silicochloroform to Acetylenes, Mar. 19, 1958, J. Am. Chem. Soc. vol. 80 pp. 5298–5300.
R. A. Benkeser et al., The Formation of 1,6–Bis(trichlorosilyl) hexane by the Chloroplatinic Acid Catalyzed Hydrosilylation of 1–Hexyne, Dec. 8, 1966, J. Org. Chem., vol. 32, pp. 2634–2636.
S. Takahashi et al., A convenient Synthesis of Ethynylarenes and Diethynylarenes, 1971, Organomet. Chem Synth. vol. 1, pp. 627–630.
R. A. Benkeser et al., The Stereochemistry of the Addition of Dichlorosilane to Acetylenes, 1974 J. Organomet. Chem. 69, 193.
K. A. Andrianov et al., Kinetics of Polyaddition Reactions of 1,1,3,3–Tetramethyldisiloxane With Ethynylbenzenes, J. Gen. Chem. USSR., vol. 44, No. 10, pp. 2102–2107, Oct. 1974.
V. B. Pukhnarevich et al., Influence of Solvents on the Rate of the Catalytic Hydrosiliiylation of 1–Hexyne with Triethlsilane, J. Gen. Chem., USSR, vol. 45, pp. 2600–2602, 1975.
V. B. Pukhnarevich et al., Relative Reactivities of Acetylenic Compounds in the Hydrosilylatin Reaction, 1975, J. Gen. Chem. USSR, 81–83.
P. H. Townsend et al., Cure Technology for Controlled Stress in Thin Benzocyclobutene Coatings, Mat. Res. Soc. Symp. Proc. vol. 264, 1992, pp. 135–140.
K. E. Bower et al., Copolymers of Substituted Acetylenes and Ethynylbenzocyclobutenes, Polymer Bulletin, vol. 27, 129–133, 1991.

Primary Examiner—Paul F. Shaver

[57] ABSTRACT

This invention relates to a novel process for preparing vinylsilane-BCBs (vinylsilane-benzocyclobutenes) comprising reacting a hydrosilating reagent with an acetylene-BCB in the presence of a catalyst.

The invention also relates to a novel mixture of isomers of DVS-bisBCB (1,3-divinyl-1,1,3,3-tetramethyldisiloxane bisbenzocyclobutene) as well as novel partially or fully cured polymers derived from the vinylsilane BCBs.

13 Claims, No Drawings

PREPARATION OF VINYLSILANE-BENZOCYCLOBUTENES

BACKGROUND OF THE INVENTION

This invention relates to a novel process for preparing vinylsilane-BCBs (vinylsilane-benzocyclobutenes), the polymers of which are useful for the preparation of multichip modules and integrated circuits.

Schrock (U.S. Pat. No. 4,812,588) describes a preparation of DVS-bisBCB (divinyltetramethyldisiloxane-bisbenzocyclobutene) involving the reaction between 4-BrBCB (3-bromobicyclo[4.2.0octa-1,3,5-triene) and DVS-(1,3-divinyl-1,1,3,3-tetramethyldisiloxane) in the presence of a palladium catalyst.

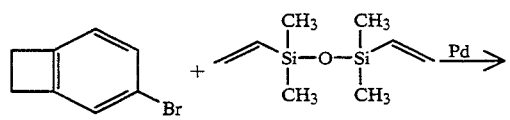

Schrock reported the product of this reaction to be the product represented by the following structure:

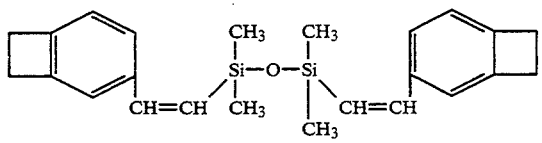

After Schrock's discovery, DeVries et al. (see 12th North American Catalyst Society Meeting, May 5-9, 1991, incorporated herein by reference) reported that the product of the reaction of 4-BrBCB and DVS under the Schrock conditions was, in fact, a mixture of isomers, predominantly the trans,trans isomer, with the trans,gem isomer being the most significant minor product:

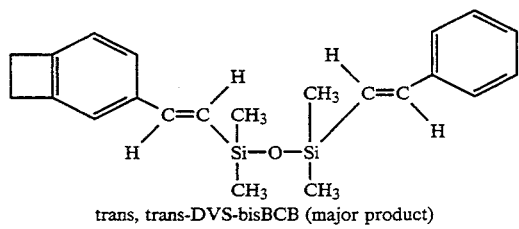
trans, trans-DVS-bisBCB (major product)

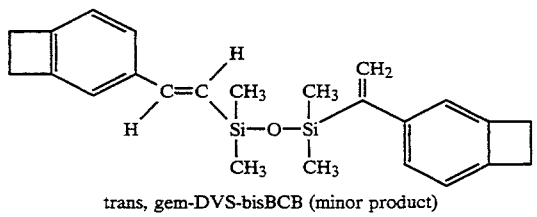
trans, gem-DVS-bisBCB (minor product)

One disadvantage of the Schrock method is that the DVS is of limited availability. A second disadvantage is that about 15 to 25% of the products of this reaction are side products. One of these side products, trans-ethylenebisbenzocyclobutene (trans- 3,3'-(1,2-ethenediyl)bis[bicyclo(4.2.0)octa-1,3,5-triene]), is formed at percent levels (see U.S. Pat. Nos. 5,243,068 and 5,136,069, incorporated herein by reference) and may sporadically crystallize out of the product mixture, thereby causing both inconsistent product and problematic processing.

Still another disadvantage of the Schrock method is that the products of the method may require treatment with peroxides and extensive purification to remove unacceptably high quantities of phosphorous, bromine, and palladium. (See DeVries et al., U.S. Pat. No. 5,138,081, incorporated herein by reference.)

In view of the deficiencies of the art, it is desirable to find a synthetic route that can produce higher yields of desired vinylsilane-BCB products, that uses more readily available materials, and that requires less workup.

SUMMARY OF THE INVENTION

The present invention is a process comprising reacting a hydrosilating reagent with an acetylene-BCB in the presence of a catalyst to form a vinylsilane-BCB.

A further aspect of the present invention is a composition comprising a vinylsilane-BCB containing less than 1 weight percent trans-ethylenebisbenzocyclobutene based on the weight of the vinylsilane-BCB.

A further aspect of the present invention is a composition comprising an isomeric mixture of DVS-bisBCBs wherein the most predominant isomer is trans, gem-DVS-bisBCB.

A further aspect of the present invention is a composition comprising a partially or fully cured polymer of a vinylsilane-BCB monomer wherein the monomer contains less than 1 weight percent trans-ethylenebisbenzocyclobutene based on the weight of the monomer.

Yet a further aspect of the present invention is a composition comprising a partially or fully cured polymer of a DVS-bisBCB isomeric mixture, wherein the isomeric mixture contains a predominance of trans,-gemDVS-bisBCB.

The present invention addresses a need in the art by making a useful product in higher yields and from more readily available starting materials than those described in the art, and by a process requiring less workup than known heretofore.

DETAILED DESCRIPTION OF THE INVENTION

In the present invention, a hydrosilating reagent is reacted with an acetylene-BCB (ethynylbicyclo[4.2.-0]octa-1,3,5-triene) to form a vinylsilane-BCB.

The acetylene-BCB may be 3-acetylene-BCB (2-ethynylbicyclo[4.2.0octa-1,3,5-triene), 4-acetylene-BCB (3-ethynylbicyclo[4.2.0octa-1,3,5-triene), an inertly substituted 3-acetylene-BCB, or an inertly substituted 4-acetylene-BCB. Any substituents that do not interfere with hydrosilation and do not poison the catalyst are acceptable. The preferred acetylene-BCBs are 3-acetylene-BCB and 4-acetylene-BCB; the more preferred acetylene-BCB is 4-acetylene-BCB.

4-Acetylene-BCB can be prepared as described by Bower and Farona (see Polymer Bulletin 27, 129–133 (1991), herein incorporated by reference), wherein 4-BrBCB (3-bromobicyclo-[4.2.01octa-1,3,5-triene) is reacted with trimethylsilylacetylene and catalytic amounts of bistriphenylphosphine palladium (II) chloride, triphenylphosphine, and cuprous iodide in the presence of a suitable solvent, such as triethylamine, to form the 1-trimethylsilyl-2-(4-benzocyclobutyl)acetylene intermediate. This intermediate is advantageously purified, preferably by distillation, to remove unreacted 4-BrBCB, then desilated with a methanolic solution of potassium carbonate to form 4-acetylene-BCB. (See also Kirchhoff et al., U.S. Pat No. 4,724,260, column 16, incorporated herein by reference.)

The 4-BrBCB can be prepared in accordance with Liu (see U.S. Pat. No. 4,822,930, herein incorporated by reference). If 4-BrBCB is prepared in this manner, some 3-BrBCB (2-bromobicyclo-[4.2.0octa-1,3,5-triene) may be formed a s a side product. Generally, this off-isomer is not separated from the 4-BrBCB. Consequently, low percent levels of 3-acetylene-BCB are typically formed in the process of preparing 4-acetylene-BCB.

3-acetylene-BCB and 4-acetylene-BCB are defined by the following structures.

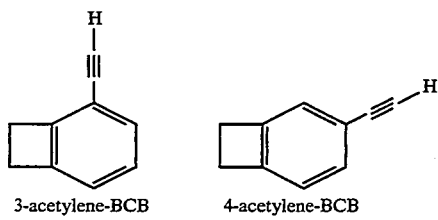

3-acetylene-BCB    4-acetylene-BCB

The term hydrosilation refers to an addition reaction in which a compound with one or more Si-H bonds adds to the acetylene group of the acetylene-BCB. Such compounds are referred to as hydrosilating reagents.

The hydrosilating reagents of the present invention have at least one Si-H bond, more preferably, one or two Si-H bonds, still more preferably not more than one Si-H bond per silicon atom, and can be linear, branched, cyclic, or polymeric. Preferred hydrosilating reagents include siloxanes, silanes, chlorosilanes, and alkoxysilanes, or mixtures thereof.

In the following discussions, the prefix alkyl is used to refer to linear, branched, cyclic, or fluorinated aliphatic groups. The term aryl refers to aromatic, heteroaromatic, or inertly substituted aromatic or heteroaromatic groups.

Preferred siloxanes are disiloxanes, including pentaalkyldisiloxanes, tetraalkyldisiloxanes, tetraaryldisiloxanes, diaryldialkyldisiloxanes, aryltrialkyldisiloxanes, and alkyltriaryldisiloxanes. More preferred disiloxanes are pentaalkyldisiloxanes, tetraalkyldisiloxanes, and tetraaryldisiloxanes. Preferred pentaalkyldisiloxanes include pentamethyldisiloxane and pentaethyldisiloxane, with pentamethyldisiloxane being more preferred; preferred tetraalkyldisiloxanes are 1,1,3,3-tetraalkyldisiloxanes, such as 1,1,3,3-tetramethyldisiloxane and 1,1,3,3-tetraethyldisiloxane, with 1,1,3,3-tetramethyldisiloxane being more preferred; the preferred tetraaryldisiloxanes are 1,1,3,3-tetraaryldisiloxanes, such as 1,1,3,3-tetraphenyldisiloxane. The most preferred disiloxane is 1,1,3,3-tetramethyldisiloxane.

Preferred silanes include trialkylsilanes, triarylsilanes, aryldialkylsilanes, alkyldiarylsilanes, dialkylsilanes, diarylsilanes, and arylalkylsilanes. Preferred trialkylsilanes include trimethylsilane and triethylsilane; a preferred triarylsilane is triphenylsilane. More preferred silanes are dialkylsilanes, such as dimethylsilane and diethylsilane; diarylsilanes, such as diphenylsilane; and arylalkylsilanes, such as ethylphenylsilane and methylphenylsilane.

Preferred chlorosilanes include polychlorosilanes, such as trichlorosilane and dichloroalkylsilanes; and monochlorosilanes, including chlorodialkylsilanes, chlorodiarylsilanes, and chloroarylalkylsilanes; with monochlorosilanes being more preferred. The preferred monochlorosilanes are chlorodialkylsilanes, such as chlorodimethylsilane and chlorodiethylsilane; and chlorodiarylsilanes, such as chlorodiphenylsilane. The most preferred monochlorosilane is chlorodimethylsilane.

Preferred alkoxysilanes include trialkoxysilanes, alkyldialkoxysilanes, dialkylalkoxysilanes, dialkoxysilanes, and alkylalkoxysilanes; with dialkylalkoxysilanes being more preferred. The preferred dialkylalkoxysilanes are dialkylethoxysilanes, with diethylethoxysilane and dimethylethoxysilane being more preferred.

The most preferred hydrosilating reagents are 1,1,3,3-tetramethyldisiloxane and chlorodimethylsilane.

The hydrosilating reagent is preferably reacted with a sufficient amount of an acetylene-BCB to convert at least one of the Si-H moieties per molecule of the hydrosilating reagent to a vinylsilane-BCB moiety. A vinylsilane-BCB is characterized by a C=C group bonded a) to an aromatic carbon of the BCB moiety; and b) to a silicon atom. The silicon atom may be geminal, cis, or trans to the BCB moiety. A vinylsilane-BCB may be represented structurally as shown:

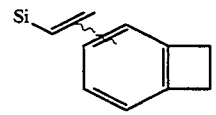

wherein the squiggly line represents a bond between the 3-or 4-position of the BCB moiety, and either carbon atom of the Si—C=C group.

The hydrosilating reagent is reacted in the presence of a catalyst, preferably with a sufficient amount of an acetylene-BCB, and under such conditions to convert all of the Si—H moieties to vinylsilane-BCB moieties.

The catalyst can be any that promotes hydrosilation. The catalyst may be, but is not restricted to, nickel, palladium, rhodium, cobalt, iron, iridium, platinum, or complexes thereof; or benzoyl peroxide. (See Harrod and Chalk, "Hydrosilation Catalyzed by Group VIII Complexes" in Wender and Pino, *Organic Syntheses via Metal Carbonyls*, John Wiley & Sons, New York, pp. 673–704, (1977), incorporated herein by reference). Of these, a complex of platinum is preferred, particularly platinum on carbon, $Pt_2(DVS)_3$ (see Lewis et al., *Organometallics*, 1991, 10, 3750, incorporated herein by reference), or chloroplatinic acid hexahydrate, (see J. L. Speier, "Homogeneous Catalyss of Hydrosilation by Transition Metals," *Adv. Organomet. Chem.*, 17, 407 (1979), incorporated herein by reference). The more preferred catalyst is chloroplatinic acid hexahydrate.

The catalyst is used in sufficient quantities to promote hydrosilation. Platinum complexes, particularly chloroplatinic acid hexahydrate and $Pt_2(DVS)_3$, can be used in quantities ranging from about $10^{-2}$ mole equivalent to about $10^{-8}$ mole equivalent, preferably from about $10^{-4}$ mole equivalent to $10^{-7}$ mole equivalent, more preferably from about $10^{-5}$ mole equivalent to about $10^{-6}$ mole equivalent based on the mole equivalents of the acetylene-BCB.

When the catalyst is a platinum complex, it is convenient to dissolve the catalyst in an unreactive solvent, then add an aliquot of the solution to the reaction mixture. The aliquot preferably comprises about 0.01 to about 1 weight percent, more preferably about 0.05 to about 0.5 weight percent of the reaction mixture, based on the weight of the reactants. Suitable solvents include, but are not restricted to, alcohols, such as ethanol, isopropanol, and butanol; glycols, such ethylene glycol and propylene glycol; and inertly substituted aromatics, such as toluene and xylene. A preferred solvent for the platinum catalyst is isopropanol.

The hydrosilation reaction can be carried out at a temperature sufficiently high to promote the reaction rate, yet sufficiently low to avoid polymerization. Because the reaction is exothermic, it may be desirable to control the rate of reaction by carrying out the reaction in the presence of sufficient quantities of a sufficiently high boiling solvent, which neither reacts with the reagent nor poisons the catalyst, to provide a reflux temperature of the reaction mixture, preferably in the range of about 50° C. to about 150° C., more preferably in the range of about 80° C. to about 125° C. Toluene is an example of a preferred solvent. The mixture is advantageously heated to a temperature suitable to initiate the exotherm, then maintained at a desired temperature, preferably the reflux temperature of the reaction. The reaction is preferably carried out substantially to completion, preferably over a period ranging from about 30 minutes to about 5 hours, more preferably from about 1 hour to about 3 hours.

The hydrosilation reaction may also be carried out in the absence of an exotherm-controlling solvent. For example, the acetylene-BCB can be added to a mixture of the hydrosilating reagent and the catalyst at a rate sufficient to control the temperature and the rate of the reaction. In this mode of addition, the reaction temperature is maintained preferably in the range of about 50° C. to about 150° C., more preferably in the range of about 80° C. to about 125° C., preferably by an external means of controlling temperature.

Because the amount of catalyst used in the reaction is so low, and because bromine-, and phosphorous-containing impurities are substantially removed in previous process steps, product workup is simplified. For example, a vinylsilane-BCB suitable for subsequent B-staging may be obtained by passing the product over silica gel. If desired, an even purer vinylsilane-BCB may be obtained by means such as distillation, preferably in vacuo distillation.

A hydrosilating reagent containing at least two Si—H moieties, preferably only two Si—H moieties, preferably a siloxane, more preferably a disiloxane, still more preferably a tetraalkyldisiloxane, and most preferably 1,1,3,3-tetramethyldisiloxane, can be reacted with sufficient quantities of an acetylene-BCB, preferably 4-acetylene-BCB, to convert all of the Si—H moieties to vinylsilane-BCB moieties; in the presence of a catalyst, preferably a platinum catalyst, more preferably chloroplatinic acid hexahydrate, at catalyst levels ranging from about $10^{-2}$ mole equivalent to about $10^{-8}$ mole equivalent, preferably from about $10^{-4}$ mole equivalent to $10^{-7}$ mole equivalent, more preferably from about $10^{-5}$ mole equivalent to about $10^{-6}$ mole equivalent based on the mole equivalents of the acetylene-BCB; maintained at a temperature sufficiently high to promote hydrosilation, yet sufficiently low to avoid polymerization, preferably at a temperature in the range of about 50° C. and about 150° C., more preferably in the range of about 80° C. and about 125° C; for a time sufficient to convert all of the Si—H moieties to vinylsilane-BCB moieties, preferably from about 30 minutes to about 5 hours, more preferably from about 1 hour to about 3 hours; to form a vinylsilane-BCB, preferably a divinyldisiloxane-bisBCB, more preferably a 1,1,3,3-tetraalkyldivinyldisiloxane-bisBCB, most preferably an isomeric mixture of DVS-bisBCBs wherein the predominant isomer is the trans,gem isomer; that contains preferably less than 1 weight percent, more preferably less than 0.5 weight percent, and most preferably less than 0.1 weight percent trans-ethylenebisbenzocyclobutene, based on the weight of the vinylsilane-BCB.

A hydrosilating reagent containing only one Si—H moiety, preferably a chlorosilane, more preferably a monochlorosilane, still more preferably a chlorodialkyl- or chlorodiarylsilane, most preferably chlorodimethylsilane; can be reacted with an acetylene-BCB, preferably 4-acetylene-BCB, preferably at about a 1:1 mole ratio of 4-acetylene-BCB to the hydrosilating reagent containing only one Si—H moiety; in the presence of a catalyst, preferably a platinum catalyst, more preferably chloroplatinic acid hexahydrate, at levels ranging from about $10^{-2}$ mole equivalent to about $10^{-8}$ mole equivalent, preferably from about $10^{-4}$ mole equivalent to $10^{-7}$ mole equivalent, more preferably from about $10^{-5}$ mole equivalent to about $10^{-6}$ mole equivalent, based on the mole equivalents of the acetylene-BCB; maintained at a temperature sufficiently high to promote hydrosilation, yet sufficiently low to avoid polymerization, preferably at a temperature in the range of about 50° C. and about 150° C., more preferably in the range of about 80° C. and about 125° C.; for a time sufficient to convert all of the Si—H moieties to vinylsilane-BCB moieties, preferably from about 30 minutes to about 5 hours, more preferably from about 1 hour to about 3 hours; to form a vinylsilane-BCB, preferably a chlorovinylsilane-BCB, more preferably a chlorodialkyl-or chlorodiarylvinylsilane-BCB, most preferably a chlorodimethylvinylsilane-BCB.

If the hydrosilating agent has more than one Si—H moiety per molecule, it may be desirable to add an amount of acetylene-BCB that is insufficient to convert all of the Si—H moieties to vinylsilane-BCB moieties. A product of this insufficient addition of acetylene-BCB to a hydrosilating reagent, preferably a dialkyl-, diaryl-, or arylalkylsilane, is preferably a dialkyl-, diaryl-, or arylalkylvinylsilane-BCB, or a mixture thereof. This product of insufficient addition of acetylene-BCB may be hydrolyzed (as described in the following paragraph) to form useful products.

In the case where the product vinylsilane-BCB contains at least one, and preferably only one, hydrolyzable group, such as an Si—H, an Si-alkoxy, or an Si—Cl group, the vinylsilane-BCB can be hydrolyzed to form a coupled product that forms presumably through a silanol intermediate.

A vinylsilane-BCB that contains an Si—Cl group can be reacted with water, preferably ice, and more preferably poured into an excess of ice, to form a coupled product, preferably a divinyldisiloxane-bisBCB. The coupled product can be isolated, for example, by extraction with a suitable solvent, such as toluene. The solvent can be removed in vacuo and the product can be optionally purified, preferably by distillation.

A vinylsilane-BCB that contains an Si—H group can be hydrolyzed in the presence of water, an alcohol, and a catalytic amount of base. The preferred alcohol is ethanol and preferred bases are sodium hydroxide and potassium hydroxide, with potassium hydroxide being more preferred. A discussion of the hydrolysis of compounds containing Si—H groups can be found in R. L.

Merker and M. J. Scott, *J. Am. Chem. Soc.*, 81, 975, (1959), incorporated herein by reference.

A vinylsilane-BCB that contains an Si-alkoxy group can be hydrolyzed in the presence of catalytic amounts of acid or base. See Pludemann, *Silane Coupling Agents*, Plenum Press, New York, pp. 32–33 and 49–73, (1982), incorporated herein by reference.

The preferred hydrolyzable vinylsilane-BCBs include chlorovinylsilane-BCBs, alkoxyvinylsilane-BCBs, dialkylvinylsilane-BCBs, diarylvinylsilane-BCBs, and arylalkylvinylsilane-BCBs, or mixtures thereof. Preferred chlorovinylsilane-BCB s are chlorodialkylvinylsilane-BCBs, such as chlorodimethylvinylsilane-BCB and chlorodiethylvinylsilane-BCB; chlorodiarylvinylsilane-BCBs, such as chlorodiphenylvinylsilane-BCB; chloroarylalkylvinylsilane-BCBs, such as chloroethylphenylvinylsilane-BCB, and chloromethylphenylvinylsilane-BCB.

Preferred alkoxyvinylsilane-BCBs include dialkylalkoxyvinylsilane-BCBs, with dialkylethoxyvinylsilane-BCBs, such as diethylethoxyvinylsilane-BCB and dimethylethoxyvinylsilane-BCB being more preferred.

Preferred dialkylvinylsilane-BCBs include dimethylvinylsilane-BCB and diethylvinylsilane-BCB; preferred diarylvinylsilane-BCBs include diphenylvinylsilane-BCB; and preferred arylalkylvinylsilane-BCBs include methylphenylvinylsilane-BCB, and ethylphenylvinylsilane-BCB.

The more preferred hydrolyzable vinylsilane-BCBs are chlorodimethylvinylsilane-BCB, chlorodiethylvinylsilane-BCB, dimethylvinylsilane-BCB, and diethylvinylsilane-BCB. The most preferred hydrolyzable vinylsilane-BCB is chlorodimethylvinylsilane-BCB.

Thus, a hydrolyzable vinylsilane-BCB, preferably a chlorovinylsilane-BCB, more preferably a chlorodialkylvinylsilane-BCB, most preferably a chlorodimethylvinylsilane-BCB, is advantageously poured over an excess of ice to form a polyalkyl-, polyaryl-, or polyalkylpolyarylpolyvinylsiloxane-poly-BCB, preferably a dialkyldiaryl-, tetraalkyl- or tetraaryldivinyldisiloxane-bisBCB, more preferably 1,1,3,3-tetramethyldivinyldisiloxane-bisBCB, 1,1,3,3-tetraphenyldivinyldisiloxane-bisBCB, or 1,1,3,3-tetraethyldivinyldisiloxane-bisBCB; most preferably an isomeric mixture of DVS-bisBCBs, wherein the trans,trans-isomer is the major product; and wherein the product of hydrolysis contains preferably less than 1 weight percent, more preferably less than 0.5 weight percent, and most preferably less than 0.1 weight percent trans-ethylenebisbenzocyclobutene based on the weight of the vinylsilane-BCB.

Mixtures of different hydrolyzable vinylsilane-BCBs can be hydrolyzed to form a variety of coupled products. For example a mixture of chlorodimethylvinylsilane-BCB and chlorodiphenylvinylsilane-BCB can be poured over an excess of ice to form a mixture of products that includes 1,1,3,3-tetramethyldivinyldisiloxane-bisBCB, 1,1,3,3-tetraphenyldivinyldisiloxane-bisBCB, and 1,1-dimethyl-3,3-diphenyldivinyldisiloxane-bisBCB.

B-staging or Curing of Vinylsilane-BCBs

The vinylsilane-BCBs of the present invention, preferably DVS-bisBCB, can be fully cured or partially cured (B-staged) in accordance with the procedures described in U.S. Pat. No. 4,642,329, herein incorporated by reference. B-staging of the vinylsilane-BCB prior to use improves handling, processing, and performance characteristics for certain applications. The consequent increase in viscosity makes the composition more suitable for thin films for multichip modules and integrated circuits.

B-staging of the vinylsilane-BCB of the invention may be achieved by subjecting the vinylsilane-BCB to polymerization conditions to provide a partially cured composition (resin) and then removing the partially cured resin from those conditions. Preferably, the monomer of the invention is B-staged in the presence of an inert gas such as nitrogen, carbon dioxide, argon, mixed inert gases, or in vacuo.

One preferred method of B-staged comprises heating the neat vinylsilane-BCB at from about 140° C. to about 200° C. for a period of time sufficient to achieve a resin viscosity which renders the resin useful for a particular application.

When B-staging of the vinylsilane-BCB is complete, a solvent, sometimes called a casting solvent, can be used to dissolve the resin and to facilitate its removal from the polymerization apparatus. Hydrocarbons are suitable casting solvents. Preferred casting solvents include xylene and mesitylene, with mesitylene being more preferred.

If the resin is to be used in a photosensitive formulation, it is most preferred to have the resin sufficiently close to the gel point (with the proviso that the resin maintains spin coatability) to achieve a soluble resin that can easily be converted into an insoluble gel when exposed to a photon source in the presence of a photosensitive crosslinking agent. B-staged resins of this type will yield the maximum solubility difference between the exposed and unexposed areas of the polymer film. Methods of preparing these types of B-staged resins include alcoholic precipitation of neat B-staged vinylsilane-BCB, and solvent assisted B-staging.

In alcoholic precipitation of neat B-staged vinylsilane-BCB, preferably DVS-bisBCB, an alcohol such as n-butanol or t-amyl alcohol is added with stirring to the solution of the neat B-staged resin in the casting solvent to form a precipitate. This precipitate can be collected, dried and redissolved in the casting solvent. The redissolved precipitate will be richer in higher molecular weight components of the partially polymerized resin.

In solvent-assisted B-staging, the vinylsilane-BCB, preferably DVS-bisBCB, is dissolved in a suitable solvent, such as mesitylene. The initial concentration of DVS-bisBCB in the solvent is preferably between about 12 and about 32 weight percent based on the weight of the solvent, more preferably between about 22 and about 27 weight percent.

Solvent-assisted B-staging is carried out, preferably in an oxygen-free atmosphere, at a temperature effective to polymerize the vinylsilane-BCB. Suitable temperatures range from about 125° C. to about 300° C., preferably from about 140° C. to about 250° C., more preferably from about 140° C. to about 200° C. If the boiling point of the solvent is less than the polymerization temperature, a pressure vessel may be used. The polymerization reaction is allowed to proceed until the desired viscosity is achieved. Solvent-assisted pre-polymerization is generally preferred over neat pre-polymerization.

The B-staged vinylsilane-BCBs, preferably the B-staged DVS-bisBCB, are useful as precursors to highly resistive, low dielectric, and hydrophobic fully cured resins suitable for integrated circuits and multichip modules.

For a preferred method of preparing fully cured DVS-bisBCB polymer coatings used for microelectronic dielectrics, see Townsend, et al., *Mat. Res. Soc. Symp. Proc.*, 2.64, pp. 135-140, (1992), incorporated herein by reference.

Example 1

DVS-bisBCB from 1,1,3,3-Tetramethyldisiloxane and 4-Acetylene-BCB

A tared 250-mL thermowell round-bottom flask equipped with a nitrogen-topped condenser, a magnetic stirrer, and a thermocouple-controlled heating mantle is charged with 1,1,3,3-tetramethyldisiloxane (69.24 g, 0.50 mole, 1.0 equivalents), 4-acetylene-BCB (132.4 g, 1.025 moles, 2.05 equivalents), toluene (20 mL), and chloroplatinic acid hexahydrate (300 $\mu$L of a 10.0 mM solution in isopropanol, 3.0 $\mu$moles, $0.6 \times 10^{-5}$ equivalents). The mixture is flushed with nitrogen, and the reaction is heated, then monitored for an exotherm after an expected induction period. The temperature rises to 125° C. before returning to the setpoint of 115° C. More catalyst is added for a total of $10^{-5}$ equivalents, and the reaction is maintained at 120° C. for two hours until capillary GC reveals less than 1 weight percent 4-acetylene-BCB and 4 weight percent mono-adducts. The ratio of major isomers in the crude mixture is 36.0 weight percent trans,trans-, 47.5 weight percent trans,-gem-, and 17.2% gem,gem-DVS-bisBCB. These DVS-bisBCB isomers comprise 90.1 weight percent of the crude product, excluding solvent.

The reaction is concentrated at 0.4 tort, and 70° C. to 100° C. to yield 200.5 g of DVS-bisBCB isomers. The crude product is distilled in a short-path wiped-film still at 106° C. and $2 \times 10^{-3}$ torr, affording 179.2 g of pale overheads (92.2% yield). The impurity trans-ethylenebisbenzocyclobutene was not detected by gas chromatography above 0.1% by weight, based on the weight of the DVS-bisBCB isomers.

Example 2

DVS-bisBCB from Chlorodimethylsilane and 4-Acetylene-BCB

A tared 250-mL thermowell round-bottom flask equipped with a nitrogen-topped condenser, a magnetic stirrer, and a thermocouple-controlled heating mantle is charged with chlorodimethylsilane (49.1 g, 509 mmoles, 1.05 equivalents), 4-acetylene-BCB (66.9 g, 484 mmoles, 1.00 equivalents), toluene (10 mL), and chloroplatinic acid hexahydrate (48 $\mu$L of a 10.0 mM solution in isopropanol, 0.48 $\mu$moles, $10^{-6}$ equivalents). The mixture is flushed with nitrogen, stirred, and gently warmed at 50° C. under nitrogen for 3 hours, and reaction is monitored for an exotherm after an expected induction period. Capillary GC reveals slow conversion, so more catalyst (a total of $3.0 \times 10^{-6}$ equivalents) is added. The temperature is slowly brought to 90° C. as the decreasing reflux rate allows. The reaction is cooled to room temperature and poured over ice water, monitoring for completion of the hydrolysis by capillary GC. The mixture is extracted with methylene chloride, and the aqueous phase back-extracted with methylene chloride (25 mL). The combined organics are washed with water, dried over $MgSO_4$, filtered, concentrated by rotary evaporation, and further concentrated at 110° C. and 0.5 torr. The concentrate has an isomer ratio of 85.8% trans,trans-, and 9.1% trans,gem-DVS-bisBCB, and 5.1% of an unidentified isomer. The DVS-bisBCB isomers comprise 84.1% of the crude product (excluding solvent, the rest being largely mono-adducts and unreacted 4-acetylene-BCB. This concentrate is distilled in a short-path wiped-film still at 160° C. and $2 \times 10^{-3}$ torr, affording 80.8 g of pale overheads (86% yield). The impurity trans-ethylenebisbenzocyclobutene was not detected by gas chromatography above 0.1% by weight, based on the weight of the DVS-bisBCB isomers.

Example 3

B-Staging DVS-bisBCB Prepared from Product of Example 1

The DVS-bisBCB from Example 1 (122 g) is heated to 170° C. with stirring under nitrogen in a reactor equipped with a viscosity probe, which is precalibrated to correlate viscosity with $M_w$ (weight average molecular weight). The reaction is allowed to proceed for 25 hours, over which time the viscosity of the sample rises to a value corresponding to an $M_w$ of about 40,000. This B-staged material is then quenched with mesitylene.

What is claimed is:

1. A process comprising reacting a hydrosilating reagent with an acetylene-BCB in the presence of a catalyst to form a vinylsilane-BCB.

2. The process of claim 1 wherein the acetylene-BCB is 4-acetylene-BCB.

3. The process of claim 2 wherein the hydrosilating reagent is a siloxane, a silane, a chlorosilane, an alkoxysilane, or a mixture thereof; and is linear, branched, cyclic, or polymeric.

4. The process of claim 3 wherein the catalyst is a platinum catalyst.

5. The process of claim 4 wherein the hydrosilating reagent is tetramethyldisiloxane, tetraethyldisiloxane, or tetraphenyldisiloxane.

6. The process of claim 5 wherein the hydrosilating reagent is tetramethyldisiloxane.

7. The process of claim 6 wherein the platinum catalyst is chloroplatinic acid hexahydrate.

8. The process of claim 4 wherein the hydrosilating reagent is chlorodiphenylsilane, chloromethylphenylsilane, chlorodiethylsilane, chlorodimethylsilane, or a mixture thereof.

9. The process of claim 4 wherein the hydrosilating reagent is diphenylsilane, diethylsilane, dimethylsilane, or a mixture thereof, and the ratio of 4-acetylene-BCB to the hydrosilating reagent is about 1:1, to form an incompletely hydrosilated vinylsilane-BCB.

10. The process of claim 4 wherein the hydrosilating reagent is trimethylsilane, triethylsilane, triphenylsilane, phenyldimethylsilane, pentamethyldisiloxane, or a mixture thereof.

11. The process of claim 10 wherein the platinum catalyst is chloroplatinic acid hexahydrate.

12. A process comprising reacting a hydrosilating reagent with an acetylene-BCB in the presence of a catalyst to form a vinylsilane-BCB that contains less than 1 weight percent trans-ethylenebisbenzocyclobutene.

13. A process for preparing a vinylsilane-BCB comprising the steps of:
 a) reacting 4-bromo-BCB with trimethylsilylacetylene to form 1-trimethylsilyl-2-(4-benzocyclobutyl)-acetylene;
 b) desilating the 1-trimethylsilyl-2-(4-benzocyclobutyl)-acetylene to form 4-acetylene-BCB; and
 c) reacting a hydrosilating agent with the 4-acetylene-BCB in the presence of a catalyst to form the vinylsilane-BCB.

* * * * *